United States Patent
Moriarty (10) Patent No.: US 9,675,445 B2
(45) Date of Patent: Jun. 13, 2017

(54) INTRAOCULAR LENS SYSTEMS AND METHODS

(71) Applicant: See Again Europe Limited, Cheshire (GB)

(72) Inventor: Brendan Joseph Moriarty, Cheshire (GB)

(73) Assignee: SEE AGAIN EUROPE LIMITED, Cheshire (GB)

(*) Notice: Subject to any disclaimer, the term of this patent is extended or adjusted under 35 U.S.C. 154(b) by 5 days.

(21) Appl. No.: 14/980,124

(22) Filed: Dec. 28, 2015

(65) Prior Publication Data

US 2016/0106535 A1 Apr. 21, 2016

Related U.S. Application Data (63) Continuation of application No. 13/322,705, filed as application No. PCT/GB2010/050868 on May 26, 2010, now abandoned.

(30) Foreign Application Priority Data

May 27, 2009 (GB) .................... 0909062.2

(51) Int. Cl.
*A61F 2/16* (2006.01)
(52) U.S. Cl.
CPC .......... *A61F 2/1648* (2013.01); *A61F 2/1602* (2013.01); *A61F 2002/1683* (2013.01); *A61F 2250/0053* (2013.01)
(58) Field of Classification Search
CPC .................... A61F 2/16; A61F 2/1648
See application file for complete search history.

(56) References Cited

U.S. PATENT DOCUMENTS

| 4,441,217 A | 4/1984 | Cozean, Jr. |
| 4,666,446 A | 5/1987 | Koziol et al. |
| 4,955,902 A | 9/1990 | Kelman |
| 5,354,334 A | 10/1994 | Fedorov et al. |
| 5,354,335 A | 10/1994 | Lipshitz et al. |

(Continued)

FOREIGN PATENT DOCUMENTS

| BE | 1016898 | 9/2007 |
| CN | 1269709 | 10/2000 |

(Continued)

OTHER PUBLICATIONS

International Written Opinion for PCT/GB2010/050868 dated Apr. 2007(6 pages).

(Continued)

*Primary Examiner* — Corrine McDermott
*Assistant Examiner* — Joshua Levine
(74) *Attorney, Agent, or Firm* — Niels Haun; Dann, Dorfman, Herrell and Skillman, P.C.

(57) ABSTRACT

An intraocular lens (31) which may be used as a posterior lens in a lens train including a converging anterior lens (20) and diverging posterior lens (31) in which the optical/focal axes of the two lenses are not coincident such that the focal point (9) of the lens train is offset from the focal axis of the anterior lens. Light rays (50) incident upon the anterior lens parallel to its focal axis may thus be directed (51) to parts of the retina offset from the fovea where the macula may not have degenerated.

30 Claims, 5 Drawing Sheets

(56) References Cited

U.S. PATENT DOCUMENTS

| | | |
|---|---|---|
| 5,391,202 A | 2/1995 | Lipshitz et al. |
| 5,814,103 A | 9/1998 | Lipshitz et al. |
| 5,876,442 A | 3/1999 | Lipshitz et al. |
| 5,928,283 A | 7/1999 | Gross et al. |
| 6,066,171 A | 5/2000 | Lipshitz et al. |
| 6,139,145 A | 10/2000 | Israel |
| 6,197,057 B1 | 3/2001 | Peyman et al. |
| 6,464,725 B2 | 10/2002 | Skotton |
| 6,569,199 B1 | 5/2003 | Dotan et al. |
| 6,596,026 B1 | 7/2003 | Gross et al. |
| 6,902,577 B2 | 6/2005 | Lipshitz et al. |
| 6,972,032 B2 | 12/2005 | Aharoni et al. |
| 7,008,448 B2 | 3/2006 | Lipshitz et al. |
| 7,060,095 B2 | 6/2006 | Ho et al. |
| 7,101,397 B2 | 9/2006 | Aharoni |
| 7,118,597 B2 | 10/2006 | Miller et al. |
| 7,186,266 B2 | 3/2007 | Peyman |
| 7,220,278 B2 | 5/2007 | Peyman |
| 7,229,476 B2 | 6/2007 | Azar |
| 7,341,599 B1 | 3/2008 | Peyman |
| 2002/0002402 A1 | 1/2002 | Tse |
| 2002/0002404 A1 | 1/2002 | Sarfarazi |
| 2002/0019667 A1 | 2/2002 | Baikoff |
| 2003/0208265 A1 | 11/2003 | Ho et al. |
| 2004/0117013 A1 | 6/2004 | Schacar |
| 2004/0148023 A1 | 7/2004 | Shu |
| 2004/0167621 A1 | 8/2004 | Peyman |
| 2005/0021138 A1 | 1/2005 | Woods |
| 2005/0060032 A1 | 3/2005 | Magnatne et al. |
| 2006/0004446 A1 | 1/2006 | Aharoni et al. |
| 2006/0100702 A1 | 5/2006 | Peyman |
| 2006/0100704 A1 | 5/2006 | Blake |
| 2006/0206206 A1* | 9/2006 | Peyman ............... A61F 2/1648 623/6.34 |
| 2006/0229720 A1 | 10/2006 | Glazier et al. |
| 2006/0259138 A1 | 11/2006 | Peyman |
| 2007/0270947 A1 | 11/2007 | Peyman |
| 2007/0276483 A1 | 11/2007 | Aharoni et al. |

FOREIGN PATENT DOCUMENTS

| | | |
|---|---|---|
| CN | 1346250 | 4/2002 |
| CN | 1384727 | 12/2002 |
| CN | 1236735 | 1/2006 |
| CN | 101090679 | 12/2007 |
| CN | 101132747 | 2/2008 |
| EP | 0682506 | 9/2002 |
| EP | 1045678 | 4/2004 |
| EP | 1045679 | 5/2004 |
| EP | 1475055 | 10/2004 |
| EP | 1082073 | 11/2004 |
| EP | 1045680 | 4/2005 |
| EP | 1229870 | 1/2007 |
| EP | 1299051 | 4/2007 |
| EP | 1859760 | 4/2010 |
| EP | 1438930 | 9/2011 |
| WO | 9012552 | 11/1990 |
| WO | 9107147 | 5/1991 |
| WO | 03082155 | 10/2003 |
| WO | 2004075729 | 9/2004 |
| WO | 2006078608 | 7/2006 |
| WO | 2007059160 | 5/2007 |
| WO | 2007109552 | 9/2007 |
| WO | 2007113832 | 10/2007 |
| WO | 2007134105 | 11/2007 |

OTHER PUBLICATIONS

International Search Report for PCT/GB2010/050868 dated Aug. 3, 2010 (4 pages).
GB Search Report dated Dec. 22, 2009 (2 pages).

* cited by examiner

FIGURE 1
THE NATURAL EYE

INTRAOCULAR LENS SYSTEMS AND METHODS

RELATED APPLICATIONS

This application is a continuation of U.S. patent application Ser. No. 13/322,705 filed on Feb. 10, 2012, which is a 371 application of International Application No. PCT/GB2010/050868 filed May 26, 2010, which claims priority to United Kingdom Patent Application No. 0909062.2 filed May 27, 2009. The foregoing applications are incorporated herein by reference.

FIELD OF THE INVENTION

The present invention relates to intraocular lenses, methods of their use and methods of their manufacture.

BACKGROUND OF THE INVENTION

Figure 1:
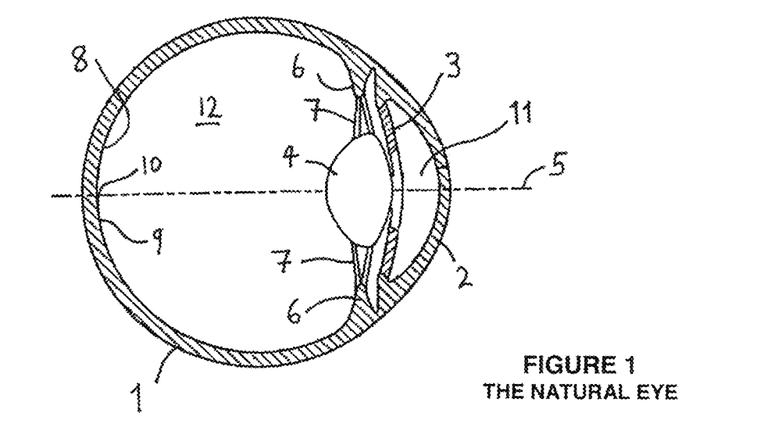
FIG. 1 illustrates a cross-sectional view of the natural (e.g. Human) eye.

FIG. 1 illustrates schematically a cross-section view of a natural eye (1) such as a human eye. The eye includes a cornea (2), an iris (3), a lens (4) defining a central optical axis (5), a ciliary sulcus (6) connected to the lens by a zonal ligament (7), a retina (8) with a macula (9) at its central region centred upon a fovea (10) where the central axis (5) of the lens intersects the retina. An anterior sac (11) is bounded by the cornea and the iris. A posterior sac (12) is bounded by the iris and the retina, and contains the lens.

Light rays (not shown) parallel to the central axis of the lens and incident upon the cornea are able to be focussed by the refractive poser of the cornea and lens incident upon the macula at the fovea of the eye. Light rays striking the cornea obliquely are unfocussed and provide less acute, peripheral vision.

Degeneration or damage of the retina at the macula (known as macular degeneration) reduces the ability of the retina to detect light incident there. This greatly reduces visual acuity by degenerating those regions of the retina upon which the eye is arranged to form focussed images. Such degeneration typically results in a blurred spot or dark spot forming at the centre of vision where, prior to degeneration, a focussed image would be. Peripheral vision remains largely unaffected.

SUMMARY OF THE DISCLOSURE

The invention aims to provide means and methods which may be useful in addressing the problem of overcoming the loss of visual acuity through macular degeneration.

In ophthalmology, the term "haptic" is used to refer to a supporting limb, arm or spring which is used to hold an artificial lens within an eye (e.g. after surgical removal of cataracts or of the natural lens for other reasons).

At its most general, the invention proposed is means and methods involving an intraocular lens which may be used as a posterior lens in a lens train (e.g. intraocular) including a converging anterior lens and diverging posterior lens in which the optical/focal axes of the two lenses are not coincident (but are preferably parallel) such that the focal point of the lens train is offset from the focal axis of the anterior lens. Light rays incident upon the anterior lens parallel to its focal axis may thus be directed to parts of the retina offset from the fovea where the macula may not have degenerated.

In a first of its aspects, the invention may provide an intraocular lens apparatus, most preferably a posterior intraocular lens apparatus, including: diverging lens means shaped to define as between opposite operative lens surfaces a lens part of minimal lens thickness surrounded by lens parts of greater lens thickness; haptic means extending from the diverging lens means to a first haptic part at an intermediate distance from the lens part of minimal lens thickness, and further extending from the diverging lens means (e.g. further extending from the first haptic part) to a second haptic part at a maximal distance from the lens part of minimal lens thickness; wherein the maximal distance is greater than the intermediate distance and the second haptic part opposes the first haptic part across the lens part of minimal lens thickness. Thus, the apparatus may have a haptic containing both the first and second haptic parts. The plane containing the two haptic parts may thus contain or incorporate the lens part of minimal lens thickness, or a part of it (e.g. focal axis at the optical centre of the lens). The haptic means may be the sole haptic attached to the diverging lens means.

The haptic means may comprise an arcuate limb incorporating the first and second haptic parts. The arcuate limb may be an arcuate spiral which spirals progressively outwardly of the diverging lens from the first haptic part to the second haptic part. The limb may be at least partly semicircular.

The first and second haptic parts may reside at diametrically opposed parts of a semicircular haptic arc connected to the diverging lens means. The haptic means may arc around the diverging lens to such an extent as to subtend about the lens part of minimal lens thickness, an angle equal to or greater than 180 degrees. In this way, a single haptic may be provided which is substantially coplanar with the plane of the diverging lens from which it extends rendering it most suitable for use as an intraocular lens in the posterior sac of the eye.

In a second of its aspects, the invention may provide an intraocular lens apparatus, most preferably a posterior intraocular lens apparatus, including: diverging lens means shaped to define as between opposite operative lens surfaces a lens part of minimal lens thickness surrounded by lens parts of greater lens thickness; a first haptic means extending from the diverging lens means to a first haptic part at a first maximal distance from the lens part of minimal lens thickness; a second haptic means separate from the first haptic means and extending from the diverging lens means to a second haptic part at a second maximal distance from the lens part of minimal lens thickness; wherein the second maximal distance is greater than the first maximal distance. Accordingly, two separate haptics may be employed and either the haptics and/or the structure of the diverging lens, may be adapted and arranged to provide the difference in the maximal distances associated with respective haptics.

According to any aspect of the invention, the lens part of minimal thickness may define a central axis perpendicular to, and passing through, opposing and instantaneously parallel operative lens surfaces. The lens part of minimal lens thickness may coincide with the optical axis of the lens which also contains the focal points of the lens. In this way, the diverging lens apparatus may be used in combination with another lens, such as a converging lens, to provide a lens train having a magnifying power. Not only may the diverging lens divert incoming light to a suitable part of the macula, but may also cooperate with an anterior lens (e.g. converging lens) to magnify the image formed by the lens train at the macula. Magnifications of up to about 1.5 are suitably provided (e.g. 1.2 to 1.4).

The first haptic part may oppose the second haptic part across the lens part of minimal lens thickness. The plane containing the two opposing haptic parts may also contain or incorporate the lens part of minimal lens thickness, or a part of it.

One or each of the first and second haptic means respectively may comprise an arcuate limb. The arcuate limb of a given haptic may be a hook shape or part spiral shape. It may extend initially away from, but subsequently towards, a periphery of the diverging lens, passing through a turning point in the limb. The first (or second) haptic part may reside at the turning point. Those parts of the haptics where the first/second haptic part reside may extent in a direction transverse to the line between the first and second haptic parts. In this way, the first/second haptic parts may present the outermost extent of the apparatus as a tangential haptic surface suitable for sliding movement against an inner wall of an eye without "snagging".

The lens part of minimal thickness may define between nearmost opposing operative lens surface, an axis perpendicular to, and passing through, both represents the optical axis of the lens containing the focal point(s) of the lens.

The lens part of minimal lens thickness may be substantially in the middle or centroid of the operative lens surface (s). For example, the diverging lens may have a substantially circular outermost periphery centred upon the lens part of minimal lens thickness. An, or each, operative lens surface may be generally symmetrical in shape and extent about the optical axis of the lens (e.g. in any radial direction therefrom).

The lens part of minimal lens thickness may be offset from the middle or centroid of the operative lens surface(s) towards a periphery thereof. For example, the diverging lens may have a substantially circular outermost periphery which is not centred upon the lens part of minimal lens thickness.

A plane containing first and second haptic parts may contain, include or intersect the lens part of minimal lens thickness.

The periphery of the diverging lens means may present a sighting means, or recognition point, indicating the peripheral part of the diverging lens means located between (e.g. in-line between) the second haptic part and the lens part of minimal lens thickness. The lens apparatus is employed as a posterior lens in a posterior aperture of the eye (ciliary sulcus), This positioning of the sighting means indicates the direction in which light will be refracted by the posterior lens when used in combination with a converging anterior lens as described below.

The first and second haptic parts may be peripheral parts (e.g. most peripheral) of the apparatus. The lens apparatus, when positioned in an anterior eye aperture, may be turned about the central axis of the aperture so as to revolve the lens part of minimal lens thickness, and the recognition point if used, about the central axis to enable the user to select a desired direction of light diversion to a desired region of the macular.

The diverging lens means may comprise a plano-concave lens, or may comprise a concavo-concave lens (e.g. bi-concave).

The diverging lens means may be flexible, preferably to an extent sufficient to permit the lens to be rolled-up and unrolled. It may be made of hard hydrophilic acrylic material such as polymethyl methacrylate (PMMA) etc, or soft hydrophilic or hydrophobic acrylic material including but not limited to polymers containing hydroxyethyl methacrylate (HEMA), silicon hydrogel, etc.

The diverging lens means may be adapted for use as a posterior intraocular lens and the apparatus may further comprise a converging lens means adapted to cooperate with the diverging lens means as an anterior intraocular lens.

The apparatus may be sold in kit form or as a kit of parts (e.g. with instructions for use) and the invention may provide a kit of parts comprising the converging and diverging lens means as described herein.

The converging lens means may include one or more haptics which extend away from the converging lens means in a direction partially transverse to the plane containing the circumference of the lens to one common side of that plane.

The converging lens means may be shaped to define as between opposite operative lens surfaces a lens part of maximal lens thickness surrounded by lens parts of lesser lens thickness and includes a third haptic means extending from the converging lens means to a third haptic part at a third maximal distance from the lens part of maximal lens thickness, and a fourth haptic means separate from the third haptic means and extending from the converging lens means to a fourth haptic part at a fourth maximal distance from the lens part of maximal lens thickness.

In a third of its aspects, the invention may provide a method of providing a lens train for forming an image of an object or scene including: providing an intraocular lens apparatus as described above; placing the converging lens means between the diverging lens means and the object or scene to be imaged such that an operative lens surface of the converging lens means opposes an operative lens surface of the diverging lens means and such that the lens part of minimal lens thickness does not oppose the lens part of maximal thickness.

The method may include providing a first (e.g. substantially circular) aperture (e.g. ciliary sulcus) in parallel opposition to a second (e.g. substantially circular) aperture (e.g. anterior sac wall circumscribing the iris) such that the centres of the first and second apertures are in register; mounting the diverging lens means within the first aperture such that haptics thereof abut opposite first aperture edges; mounting the converging lens means within the second aperture such that haptics thereof abut opposite second aperture edges.

The method may include rotating the mounted diverging lens means within the first aperture thereby to revolve the lens part of minimal lens thickness about the centre of the first aperture thereby to select the location of images formable by the lens train in use.

In a fourth of its aspects, the invention may provide a method of manufacturing an intraocular lens (preferably a posterior intraocular lens) such as is described above including: providing a lens template; shaping (e.g. lathing) inner surface parts of the lens template to define opposite surfaces of a lens (e.g. concave or bi-concave) between which is defined a lens part of minimal lens thickness surrounded by lens parts of greater lens thickness; shaping (e.g. milling or cutting) outer surface parts of the lens template around said inner surface parts to form said diverging lens means and said haptic(s). The operative lens surfaces may be polished after being shaped.

The method may include shaping portions of said inner surface parts defining said lens to form said diverging lens means and said haptic(s).

The method may include shaping said inner surface parts to form a symmetrical concavity with a circular periphery centred upon the lens part of minimal lens thickness and forming therefrom the diverging lens means with a lens periphery centred upon other than the lens part of minimal lens thickness.

The lens train described above may possess an axial offset ($\Delta$) resulting from an axial offsetting of the focal axis of the posterior and anterior lenses by between about 0.5 m and 2.0 mm. The angular deviation of the focal point of the lens train relative to the furthest focal point of the diverging (posterior) lens may be upto about 15 degrees. The anterior converging lens may have a positive power of between about 50 and 60 dioptres (e.g. +53 dioptres). The posterior lens may be located within the focal length of the anterior lens, and the anterior lens may be located within the focal length of the posterior lens. The anterior lens (excluding haptic lengths) may be between about 4 mm and 7 mm (e.g. 5 mm) in diameter. Haptics may extend to a maximal distance from opposite edges of the anterior lens of between 3 mm and 6 mm (e.g. 4 mm) therefrom each. The diverging lens may have a negative optical power of between about −55 and −70 dioptres (e.g. −64 dioptres). The diverging lens may be between 5 mm and 9 mm (e.g. 7 mm) in diameter and may have a lesser haptic (containing the first haptic part) extending from the edge of the diverging lens to a maximal distance of between about 1.5 and 3 mm (e.g. 2 mm) therefrom. The diverging lens may have a greater haptic (containing the second haptic part) extending from the (e.g. opposite edge of the) posterior lens to a maximal distance of between about 3 mm and 6 mm (e.g. 4 mm) therefrom. The diverging lens unit may be between about 10 m and 16 mm (e.g. 13 mm) across at its widest point.

BRIEF DESCRIPTION OF THE DRAWINGS

There now follows a description of some illustrative, but non-limiting and non-exhaustive, examples of embodiments of the invention with reference to the drawings of which.

In the drawings, like items are assigned like reference symbols.

DETAILED DESCRIPTION

Figure 2A:
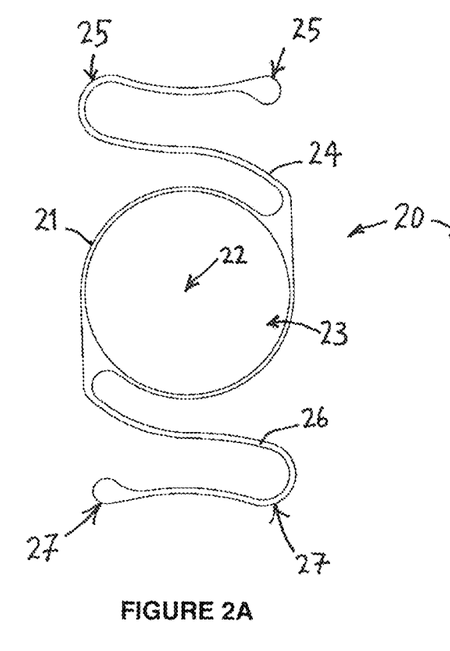
FIGS. 2A and 2B illustrate a plan view (FIG. 2A) and a side view (FIG. 2B) of an anterior intraocular lens apparatus with symmetrical haptics.
Figure 2B:
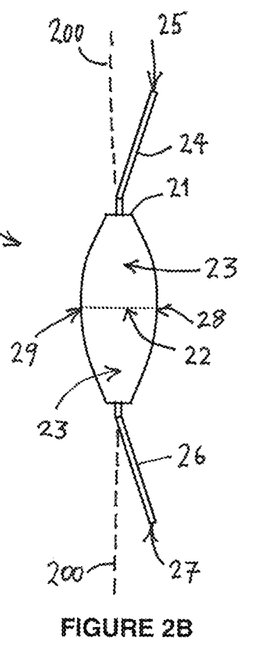

FIGS. 2A and 2B illustrate views of an anterior intraocular lens unit (20) including a converging lens (21) shaped to define as between opposite operative anterior lens surfaces a lens part of maximal thickness (22) surrounded by lens parts of lesser lens thickness (23). The lens part of maximal thickness defines a central axis perpendicular to, and passing through, opposing and instantaneously parallel operative anterior lens surfaces (28, 29). This axis coincides with the optical axis of the converging lens which also contains the focal points of the lens.

The anterior lens unit has a first serpentine anterior haptic limb (24) extending away from the converging lens to a first anterior haptic part (25) at a first anterior maximal distance from the lens part of maximal lens thickness. A second serpentine anterior haptic limb (26) separate from the first anterior haptic limb, extends from a part of the converging lens diametrically opposed to that part from which the first serpentine anterior haptic limb extends, and so extends to a second anterior haptic part (27) at a second anterior maximal distance from the lens part of maximal lens thickness. The first and second anterior maximal distances are substantially equal. At their maximal distances, the first and second anterior haptic parts are defined by respective haptic limb parts which are generally oriented in a direction tangential to a bounding circle geometrically bounding the anterior lens unit and centred upon the central axis of the converging lens. Accordingly, the outermost parts of the anterior lens unit are equidistant from the central axis and opposed across it.

They present osculating and locally parallel abutting surfaces to the inner circular edge of a circular aperture corresponding to the bounding circle (e.g. an aperture in the eye). The serpentine nature of the haptic limbs provides a resilience or springiness via which the anterior lens unit may hold the converging lens centrally in registered with such an aperture.

Each of the anterior haptics extends away from the converging lens in a direction oblique to (i.e. partly parallel to, and partially transverse to) the plane (200) containing the circumference of the lens to one common side of that plane. As a result, the anterior lens is adapted to be placed within the anterior sac of the eye (4) over, and centrally in register with, the aperture of the iris (3).

Figure 3A:
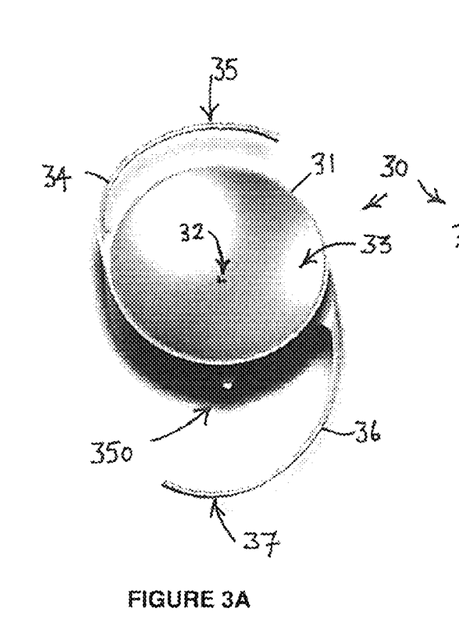
FIGS. 3A and 3B illustrate a plan view (FIG. 3A) and a side view (FIG. 3B) of a posterior intraocular lens apparatus with asymmetrical haptics.
Figure 3B:
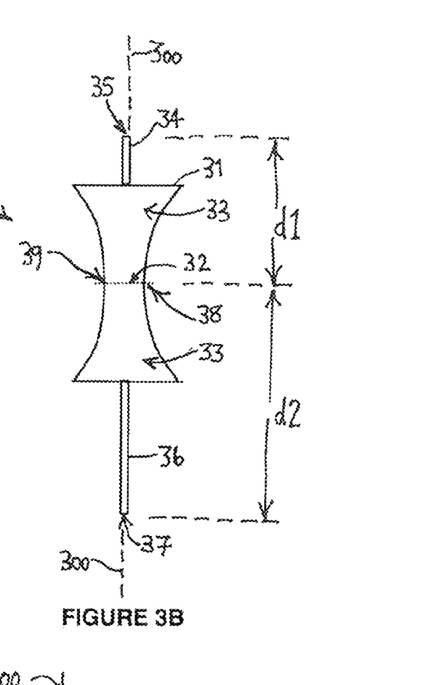

FIGS. 3A and 3B show views of a posterior intraocular lens unit (30) including a diverging lens (31) shaped to define as between opposite operative lens surfaces a lens part of minimal lens thickness (32) surrounded by lens parts of greater lens thickness (33). The posterior lens unit has a first arcuate posterior haptic (34) extending from the diverging lens to a first posterior haptic part (35) at a first posterior maximal distance (d1) from the lens part of minimal lens thickness. A second arcuate posterior haptic (36), separate from the first posterior haptic, extends away from a part of the diverging lens diametrically opposed to that part from which the first arcuate posterior haptic extends, and so extends to a second posterior haptic part (37) at a second posterior maximal distance (d2) from the lens part of minimal lens thickness.

The second posterior maximal distance is greater than the first posterior maximal distance (i.e. d2>d1). At their maximal distances, the first and second posterior haptic parts are defined by respective arcuate haptic limb parts which are generally oriented in a direction tangential to a bounding circle geometrically bounding the posterior lens unit and offset from the central axis of the diverging lens. Accordingly, the outermost parts of the posterior lens unit are opposed across the centre of the bounding circle the central axis. However, while those parts are equidistant from the centre of the bounding circle, they are not equidistant from the central axis of the diverging lens such that the central axis is offset from the centre of the bounding circle. They present osculating and locally parallel abutting surfaces to the inner circular edge of a circular aperture corresponding to the bounding circle (e.g. an aperture in the eye). The arcuate nature of the haptic limbs provides a resilience or springiness via which the posterior lens unit may hold the diverging lens within such an aperture with the central axis of the lens axially offset from the centre of the aperture.

FIG. 3B shows the lens unit of FIG. 3A in side view schematically and showing the diverging lens in cross-sectional view to illustrate curvature, while the haptics are shown in full side view to illustrate the radial extent to which they extend or project from the lens part of minimal thickness (32).

The lens part of minimal thickness defines a central axis perpendicular to, and passing through, opposing and instantaneously parallel operative lens surfaces (38, 39). This axis coincides with the optical axis of the lens which also contains the focal points of the lens.

Each of the posterior haptics extends away from the diverging lens in a direction parallel to, and within, the plane (300) containing the circumference of the lens. As a result, the anterior lens is adapted to be placed within the posterior sac of the eye (12) behind the aperture of the iris and in place of the natural lens (4) of the eye.

Figures 4A, 4B:
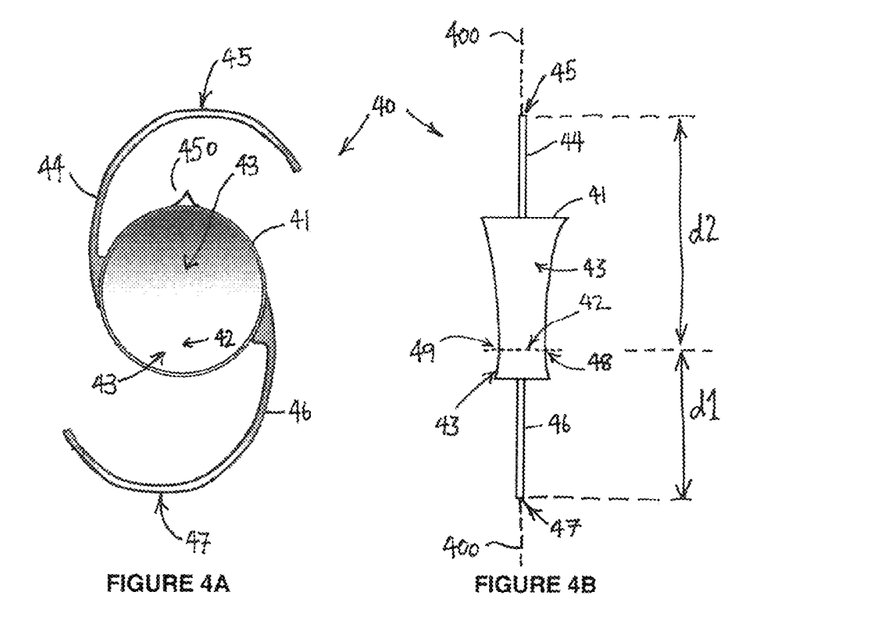
FIGS. 4A and 4B illustrate a plan view (FIG. 4A) and a side view (FIG. 4B) of a posterior intraocular lens apparatus symmetrical haptics.

FIGS. 4A and 4B show views of another embodiment of a posterior intraocular lens unit (40) including a diverging lens (41) shaped to define as between opposite operative lens surfaces a lens part of minimal lens thickness (42) surrounded by lens parts of greater lens thickness (43). The posterior lens unit has a first arcuate posterior haptic (44) extending from the diverging lens to a first posterior haptic part (45) at a first posterior maximal distance (d2) from the lens part of minimal lens thickness. A second arcuate posterior haptic (46), separate from the first posterior haptic, extends away from a part of the diverging lens diametrically opposed to that part from which the first arcuate posterior haptic extends. It so extends to a second posterior haptic part (47) at a second posterior maximal distance (d1) from the lens part of minimal lens thickness. The second posterior maximal distance is less than the first posterior maximal distance (i.e. d2>d1).

The first and second posterior haptics (44,45) are substantially of equal length. At their maximal distances, which do not coincide with their ends, the first and second posterior haptic parts are defined by respective arcuate haptic limb parts which are generally oriented in a direction tangential to a bounding circle (locus) geometrically defining the extreme limits of the posterior lens unit and notionally bounding it. The geometrical centre of the bounding circle does not coincide with the central axis (42) of the diverging lens. As a result, the outermost parts of the posterior lens unit (45, 47) are opposed to each other across the centre of the bounding circle the central axis of the lens. Those parts are equidistant from the centre of the bounding circle. They are not also equidistant from the central axis (42) of the diverging lens. The central axis is thereby offset from the centre of the bounding circle. The extreme haptic parts of the lens unit present abutting surfaces which are arranged to be locally parallel to the inner circular edge of a circular aperture corresponding to the bounding circle (e.g. an aperture in the eye). The arcuate spiral nature of the haptic limbs provides a resilience or springiness via which the posterior lens unit may hold the diverging lens within such an aperture with the central axis of the lens axially offset from the centre of the aperture.

FIG. 4B shows the lens unit of FIG. 4A in side view schematically and showing the diverging lens in cross-sectional view to illustrate curvature, while the haptics are shown in full side view to illustrate the radial extent to which they extend or project from the lens part of minimal thickness (42). The condition d2>d1 applicable to this lens (both FIGS. 4A and 4B) can be seen explicitly.

The lens part of minimal thickness defines a central axis perpendicular to, and passing through, opposing and instantaneously parallel operative lens surfaces (48, 49). This axis coincides with the optical axis of the lens which also contains the focal points of the lens.

Each of the posterior haptics extends away from the diverging lens in a direction parallel to, and within, the plane (400) containing the circumference of the lens. As a result, the anterior lens is adapted to be placed within the posterior sac of the eye (12) behind the aperture of the iris and in place of the natural lens (4) of the eye.

Figure 5:
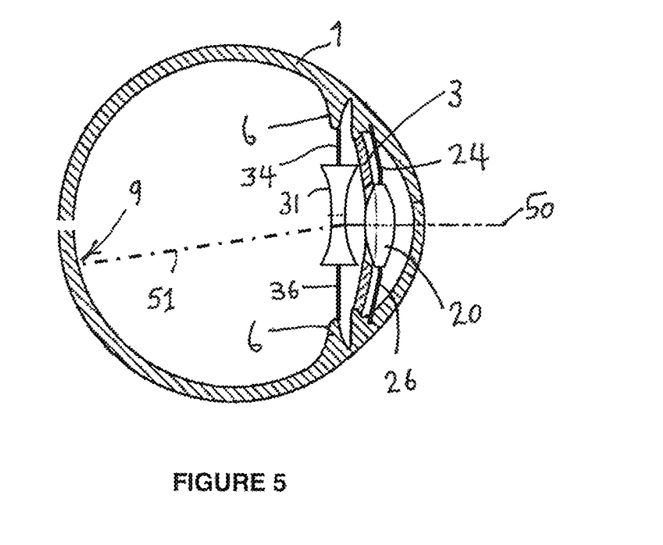
FIG. 5 illustrates a cross-sectional view of the natural (e.g. Human) eye including an anterior intraocular lens apparatus of FIGS. 2A and 2B in the anterior sac and a posterior intraocular lens apparatus of FIGS. 3A and 3B in the posterior sac in place of the natural lens.

The first and second arcuate posterior haptics of FIGS. 3A, 3B, 4A and 4B are shaped as spiral arms which extend from and around the lens about its central axis in a common angular sense subtending about 90 degrees from end to end at the lens centre. Between the outermost haptic part and the terminal end of each haptic limb, the limb approaches the lens. Furthermore, peripheral outermost edge of the converging lens, in each case, presents a sighting lug (350, 450) in-line with the line containing the outermost posterior haptic parts and the central axis of the lens. The sighting lug, or recognition point, indicates the direction, relative to the central axis, in which light emanating from the anterior lens will be directed when the posterior and anterior lens units are co-arranged in the manner illustrated in FIGS. 5 and 6. Furthermore, in embodiments of the invention such as shown in FIGS. 3A and 3B and 5, haptics extend by differing amounts from the local lens periphery. By locating the sighting lug at the lens periphery facing the longer of the two haptics (36), the user is better able to see the sighting lug via the aperture of the iris when the posterior lens unit is being positioned there. For example, the haptic dimension may be chosen such that the sighting lug is adjacent, or just below, an edge of the iris when the eye is viewed externally.

FIG. 5 schematically illustrates a cross-section view of an eye (1) in which an anterior lens unit (20) of the type illustrated in FIGS. 2A and 2B is inserted into the anterior sac (11) of the eye centrally in register with the centre of the aperture of the iris (3). The serpentine anterior haptics (24, 26) abut the circular wall parts of the eye immediately adjacent parts thereof to which the iris is attached. This abutment holds the anterior lens in place. A posterior lens unit (30) of the type illustrated in FIGS. 3A and 3B is inserted into the circular aperture defined by the ciliary sulcus (6) in place of the zonular ligament (7) and the natural lens (4). The posterior spiral haptics of the posterior lens hold the posterior lens in place against the ciliary sulcus. As a result, the central axis of the anterior lens is axially offset from the central axis of the posterior lens. Light rays (50) entering the eye parallel to the central axis of the anterior lens pass therethrough to the posterior lens to be refracted by (51) it to a focal point on the macular offset from the fovea and of un-degenerated condition.

Figure 6:
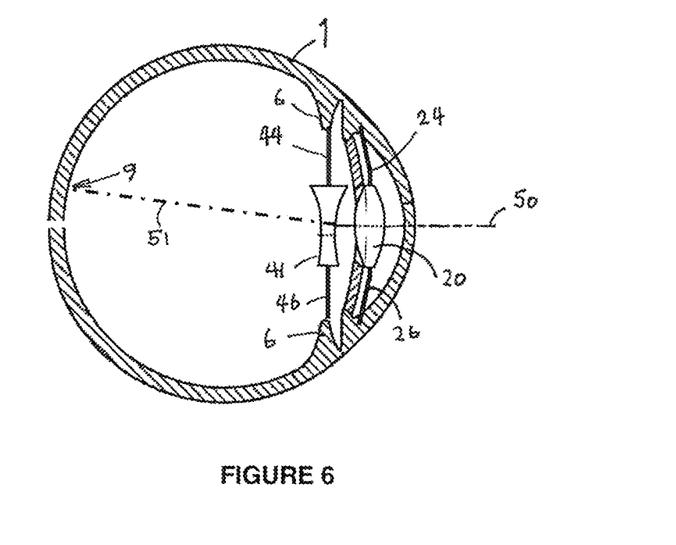
FIG. 6 illustrates a cross-sectional view of the natural (e.g. Human) eye including an anterior intraocular lens apparatus of FIGS. 2A and 2B in the anterior sac and a posterior intraocular lens apparatus of FIGS. 4A and 4B in the posterior sac in place of the natural lens.

FIG. 6 schematically shows the same arrangement as shown in FIG. 5 except that the posterior lens is a posterior lens of the type illustrated in FIGS. 4A and 4B.

In the arrangements illustrated in FIGS. 5 and 6, the optical train provided by the anterior and posterior lenses is such that the central axes of the two lenses are substantially parallel, though axially offset.

Figure 7:
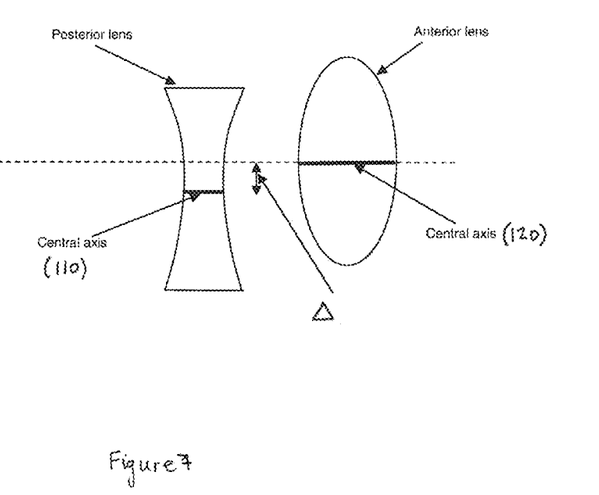
FIG. 7 schematically illustrates an optical train comprising an anterior converging lens and a posterior lens with central axes relatively offset.
Figure 8:
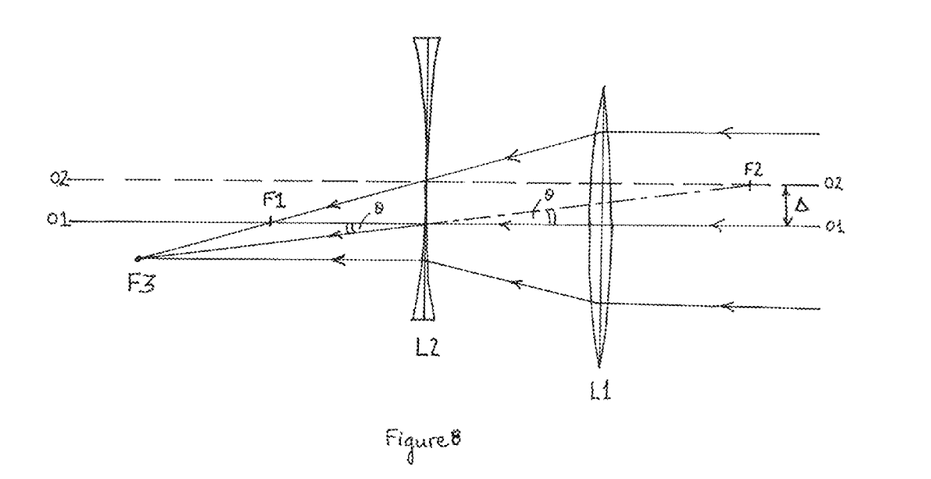
FIG. 8 schematically illustrates an optical train comprising an anterior lens and a posterior diverging lens with central axes relatively offset and the resulting axial offsetting of images formed thereby.

FIG. 7 schematically illustrates the relationship between anterior converging (20) and posterior diverging (30) lenses in the lens train of preferred embodiments of the invention (haptics not shown). The dimensions of the lenses are exaggerated. An axial offset (Δ) results in the axial offsetting of the focal point of the lens train as illustrated in FIG. 8. The anterior converging lens (L1) has a positive power (e.g. +53 dioptres) and a focal point (F1) located upon the central axis (O1) of the lens. The anterior lens may be 5 mm in diameter. Symmetrical haptics (not shown) may extend to a maximal distance from opposite edges of the lens of 4 mm therefrom each (e.g. the anterior converging lens unit may be 13 mm across at its widest point). The posterior diverging lens (L2) has a negative optical power (e.g. −64 dioptres) and a focal point (F2) located upon its central axis (O2). The posterior lens may be 7 mm in diameter and may have a lesser haptic (not shown) extending from the edge of the posterior lens to a maximal distance of 2 mm therefrom, and a greater haptic (not shown) extending from the opposite edge of the posterior lens to a maximal distance of 4 mm therefrom (e.g. the posterior diverging lens unit may be 13 mm across at its widest point).

The central axis (O2) of the posterior lens is parallel to the central axis (O1) of the anterior lens and axially offset therefrom by a displacement Δ (e.g. between 0.5 and 2 mm, such as 1 mm). The posterior lens is located between the anterior lens and the focal point (F1) of the anterior lens. The anterior lens is located between the posterior lens and the focal point (F2) of the posterior lens. Light rays incident upon the anterior lens parallel to its central axis are focussed by the lens train at a focal point (F3) offset from the central axis (O1) of the anterior lens rays in a direction opposite to the axial offset (Δ) of the central axis (O2) of the posterior lens.

Since, in the so-called "thin lens approximation", an axially parallel light ray incident upon the anterior lens surface (L1) at its lens part of maximum lens thickness must pass through the lens un-refracted, and must then be refracted by the posterior lens (L2) in a direction which must trace back to the focal point (F2) of the posterior lens, the angular deviation (θ) of the focal point (F3) of the lens train from the central axis (O1) of the anterior lens is given by:

$$\Theta = \arctan(\Delta/f_2)$$

where $f_2$ is the focal length of the posterior diverging lens (L2). Of course, thick lenses may be employed which may not entirely conform to this relation, and the approximation of thin lenses upon which it is based, but in general the deviation of the focal point (F3) of the lens train is in proportion to, and oppositely directed to, the axial offset of the lenses. The angular deviation (Θ) may be about 15 degrees.

Figure 9:
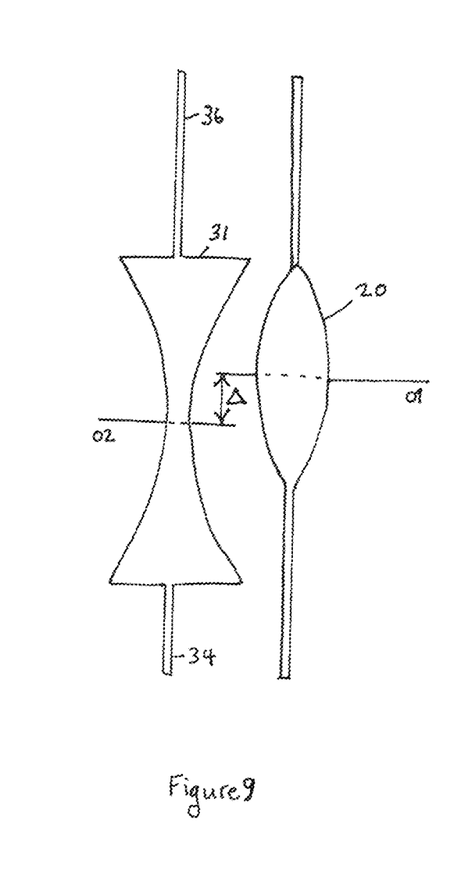
FIGS. 9 and 10 schematically illustrate examples of an optical train comprising an anterior converging lens apparatus and a posterior diverging lens apparatus with central axes relatively offset by virtue of asymmetric haptics or asymmetric posterior lens structures.
Figure 10:
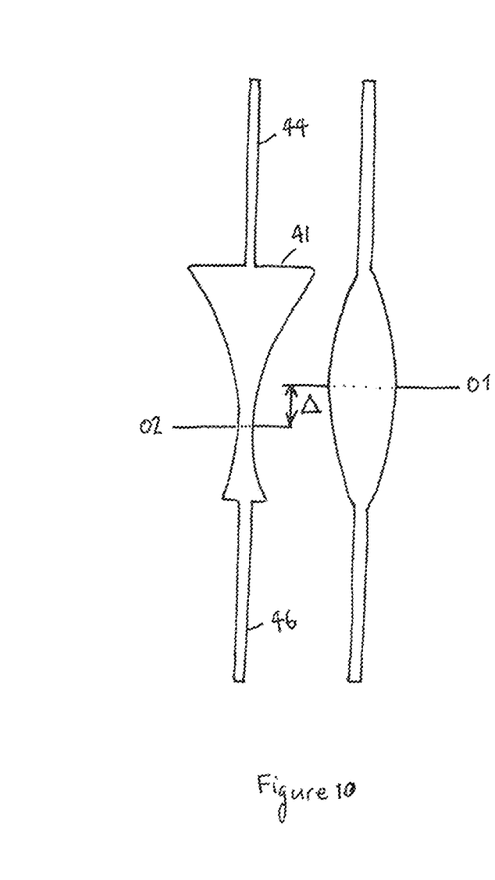

FIGS. 9 and 10 illustrate schematically the lens train of FIGS. 7 and 8 with different haptic and posterior lens designs to achieve axial offset.

Thus, a lens train may be provided for forming an image of an object or scene at an un-degenerated part of the macula.

A first substantially circular aperture is provided by the periphery of the ciliary sulcus and in parallel opposition to that a second substantially circular aperture is provided by the eye wall parts where the iris meets the eye wall. The centres of the first and second apertures are in register naturally. First the diverging posterior lens unit may be mounted within the first aperture, such that haptics thereof abut opposite first aperture edges. The posterior lens be rotated/revolved within the first aperture to revolve the lens part of minimal lens thickness about the centre of the first aperture. This revolves the focal point (3) of the lens train ultimately provided when the anterior lens is put in place. Accordingly, a selection of the location, on the retina, of images formable by the lens train in use may be made until an optimal part of the retina is found.

Completion of the lens train is then done by mounting the converging anterior lens within the second aperture such that haptics thereof abut opposite second aperture edges.

The lens train may provide a magnification factor of between 1.0 and 1.5 (e.g. 1.2 to 1.4).

The posterior lens unit, and optionally the anterior lens unit may be made of hard hydrophilic acrylic material such as polymethyl methacrylate (PMMA) etc, or soft hydrophilic or hydrophobic acrylic material including but not limited to polymers containing hydroxyethyl methacrylate (HEMA), silicon hydrogel, etc.

Accordingly, the posterior lens, and/or the anterior lens, may be rolled-up before being inserted into the eye through a small incision, thereafter to be unfurled and positioned within the eye as required.

Manufacturing the posterior intraocular lens such as is described above, may comprise: providing a lens template; lathing inner surface parts of opposite sides of the lens template to define circular, concave opposite surface regions providing a lens between which is defined a lens part of minimal lens thickness corresponding to the central axis of the lens (on which the focal point of the lens resides); milling away outer parts of the lens template around and up to the edge of the concave inner lens surface parts to form the outer periphery of the diverging lens and the haptics which extend from it. The lens central axis may correspond to the middle of the lathed concave surfaces when the milling does not remove any such lathed parts. FIGS. 3A and 3B is an example.

The method may include forming the outer lens periphery by milling away lathed portions of the concave inner lens surface to form the diverging lens and the haptic(s) extending from its edges. The remaining concave lens may then have a circular periphery enclosing the central axis offset from the middle of the lathed concave surfaces remaining. FIGS. 4A and 4B is an example.

The examples described herein are intended as non-limiting and variations and modification such as would be readily apparent to the skilled person are encompassed by the scope of the invention such as is defined by the claims.

The invention claimed is:

1. A method of providing an intraocular lens train for forming in an eye an image of an object or scene external to the eye including:
    providing a posterior intraocular lens apparatus including:
        a diverging lens shaped to define as between opposite operative lens surfaces a lens part of minimal lens thickness surrounded by lens parts of greater lens thickness;
        a haptic extending from the diverging lens to a first haptic distal part at an intermediate distance from the lens part of minimal lens thickness, and further extending from the diverging lens to a second haptic distal part at a maximal distance from the lens part of minimal lens thickness;

wherein the maximal distance is greater than the intermediate distance and the second haptic part opposes the first haptic part across the lens part of minimal lens thickness;

providing an anterior intraocular lens apparatus including:
a converging lens adapted to cooperate with the diverging lens;

positioning the diverging lens in the posterior sac of the eye using said haptic;

positioning the converging lens in the anterior sac of the eye between the diverging lens and the object or scene to be imaged such that an operative lens surface of the converging lens opposes an operative lens surface of the diverging lens, and such that the lens part of minimal lens thickness of the diverging lens does not oppose the centre of the converging lens.

2. A method according to claim 1 in which the haptic comprises an arcuate limb incorporating the first and second haptic parts.

3. A method of providing an intraocular lens train according to claim 1 in an eye comprising a ciliary sulcus defining a first substantially circular aperture in parallel opposition to a second substantially circular aperture defined by the anterior sac wall circumscribing the iris such that the centres of the first and second apertures are in register, the method comprising;
mounting the diverging lens at the first aperture such that haptics thereof abut opposing first aperture edges;
mounting the converging lens at the second aperture such that haptics thereof abut opposing second aperture edges.

4. A method according to claim 3 including rotating the mounted diverging lens within the first aperture thereby to revolve the lens part of minimal lens thickness about the centre of the first aperture thereby to select the location of images formable by the lens train in use.

5. A method according to claim 1 in which the one or each of the first and second haptic respectively comprises an arcuate limb.

6. A method according to claim 1 in which the lens part of minimal lens thickness is substantially in the middle of the operative lens surface(s).

7. A method according to claim 1 in which the lens part of minimal lens thickness is offset from the middle of the operative lens surface(s) towards a periphery thereof.

8. A method according to claim 1 in which a plane containing first and second haptic parts contains the lens part of minimal lens thickness.

9. A method according to claim 1 in which the periphery of the diverging lens presents a sighting part indicating the peripheral part of the diverging lens located between the second haptic part and the lens part of minimal lens thickness.

10. A method according to claim 1 in which the first and second haptic parts are peripheral parts of the apparatus.

11. A method according to claim 1 in which the diverging lens comprises a plano-concave lens.

12. A method according to claim 1 in which the diverging lens comprises a concavo-concave lens.

13. A method according to claim 1 wherein in which the diverging lens is flexible.

14. A method according to claim 1 in which the converging lens includes one or more haptics which extend away from the converging lens in a direction partially transverse to the plane containing the circumference of the lens to one common side of that plane.

15. A method according to claim 1 in which the converging lens is shaped to define as between opposite operative lens surfaces a lens part of maximal lens thickness surrounded by lens parts of lesser lens thickness and includes a third haptic extending from the converging lens to a third haptic part at a third maximal distance from the lens part of maximal lens thickness, and a fourth haptic separate from the third haptic and extending from the converging lens to a fourth haptic part at a fourth maximal distance from the lens part of maximal lens thickness.

16. A method of providing an intraocular lens train for forming in an eye an image of an object or scene external to the eye including:
providing a posterior intraocular lens apparatus including:
diverging lens shaped to define as between opposite operative lens surfaces a lens part of minimal lens thickness surrounded by lens parts of greater lens thickness;
a first haptic extending from the diverging lens to a first haptic distal part at a first maximal distance from the lens part of minimal lens thickness;
a second haptic separate from the first haptic and extending from the diverging lens to a second distal haptic part at a second maximal distance from the lens part of minimal lens thickness;
wherein the second maximal distance is greater than the first maximal distance;
providing an anterior intraocular lens apparatus including:
a converging lens adapted to cooperate with the diverging lens;
positioning the diverging lens in the posterior sac of the eye using said first haptic and said second haptic;
positioning the converging lens in the anterior sac of the eye between the diverging lens and the object or scene to be imaged such that an operative lens surface of the converging lens opposes an operative lens surface of the diverging lens, and such that the lens part of minimal lens thickness of the diverging lens does not oppose the centre of the converging lens.

17. A method according to claim 16 in which the first haptic part opposes the second haptic part across the lens part of minimal lens thickness.

18. A method of providing an intraocular lens train according to claim 16 in an eye comprising a ciliary sulcus defining a first substantially circular aperture in parallel opposition to a second substantially circular aperture defined by the anterior sac wall circumscribing the iris such that the centres of the first and second apertures are in register, the method comprising;
mounting the diverging lens at the first aperture such that haptics thereof abut opposing first aperture edges;
mounting the converging lens at the second aperture such that haptics thereof abut opposing second aperture edges.

19. A method according to claim 18 including rotating the mounted diverging lens within the first aperture thereby to revolve the lens part of minimal lens thickness about the centre of the first aperture thereby to select the location of images formable by the lens train in use.

20. A method according to claim 16 in which the one or each of the first and second haptic respectively comprises an arcuate limb.

21. A method according to claim 16 in which the lens part of minimal lens thickness is substantially in the middle of the operative lens surface(s).

22. A method according to claim 16 in which the lens part of minimal lens thickness is offset from the middle of the operative lens surface(s) towards a periphery thereof.

23. A method according to claim 16 in which a plane containing first and second haptic parts contains the lens part of minimal lens thickness.

24. A method according to claim 16 in which the periphery of the diverging lens presents a sighting part indicating the peripheral part of the diverging lens located between the second haptic part and the lens part of minimal lens thickness.

25. A method according to claim 16 in which the first and second haptic parts are peripheral parts of the apparatus.

26. A method according to claim 16 in which the diverging lens comprises a plano-concave lens.

27. A method according to claim 16 in which the diverging lens comprises a concavo-concave lens.

28. A method according to claim 16 wherein in which the diverging lens is flexible.

29. A method according to claim 16 in which the converging lens includes one or more haptics which extend away from the converging lens in a direction partially transverse to the plane containing the circumference of the lens to one common side of that plane.

30. A method according to claim 16 in which the converging lens is shaped to define as between opposite operative lens surfaces a lens part of maximal lens thickness surrounded by lens parts of lesser lens thickness and includes a third haptic extending from the converging lens to a third haptic part at a third maximal distance from the lens part of maximal lens thickness, and a fourth haptic separate from the third haptic and extending from the converging lens to a fourth haptic part at a fourth maximal distance from the lens part of maximal lens thickness.

* * * * *